United States Patent [19]

Nakajima et al.

[11] Patent Number: 5,300,654
[45] Date of Patent: Apr. 5, 1994

[54] METHOD FOR THE PREPARATION OF UNSATURATED KETONES

[75] Inventors: Masashi Nakajima; Tadashi Kyotani; Mikio Sawaki, all of Takaoka, Japan

[73] Assignee: Nippon Soda Co., Ltd., Ohtemachi, Japan

[21] Appl. No.: 730,844

[22] PCT Filed: Nov. 15, 1990

[86] PCT No.: PCT/JP90/01489
§ 371 Date: Jul. 15, 1991
§ 102(e) Date: Jul. 15, 1991

[87] PCT Pub. No.: WO91/07368
PCT Pub. Date: May 30, 1991

[30] Foreign Application Priority Data

Nov. 17, 1989 [JP] Japan .................. 1-297389

[51] Int. Cl.$^5$ .............. C07C 45/64; C07C 45/66; C07D 309/06; C07D 335/02
[52] U.S. Cl. .................. 549/13; 549/427; 549/497; 568/42; 568/43; 568/306; 568/308; 568/313; 568/343; 568/345; 568/376; 568/388; 568/390; 568/417
[58] Field of Search ........... 549/13, 427, 356, 497, 549/429; 568/308, 306, 313, 42, 43, 345, 376, 390, 417, 312, 343, 388

[56] References Cited

U.S. PATENT DOCUMENTS 2,088,015  7/2937  Wickert .................. 568/417
4,355,184  10/1982  Kaku et al. ............. 568/397

FOREIGN PATENT DOCUMENTS 845649  11/1938  France .
471483  3/1937  United Kingdom .

OTHER PUBLICATIONS

M. Stiles, et al., *J. Am. Chem. Soc.*, "Catalyst Selectivity in the Reactions of Unsymmetrical Ketones," 81, pp. 628–632 (1959).
V. Chandrasekharan, et al., *Indian Journal of Chemistry*, "Synthesis of 5-Alkyl & 5-Aryl-resorcinols", 16B, pp. 970–972 (1978).
H. Rupe et al., *Ber.*, "Uber die Einwirkung von Semicarbazid auf ungesattigte Verbindungen," 40, pp. 6764–6770 (1907).

*Primary Examiner*—Richard L. Raymond
*Attorney, Agent, or Firm*—Joseph C. Mason, Jr.; Ronald E. Smith; George B. Oujevolk

[57] ABSTRACT

β-hydroxyketones are prepared by reacting an aldehyde with acetone in the presence of perhydroisoindole or pyrrolidine and water. The resulting β-hydroxyketone is further reacted in the presence of a solvent mixture to produce α-β-unsaturated ketones.

3 Claims, No Drawings

METHOD FOR THE PREPARATION OF UNSATURATED KETONES

FIELD OF INVENTION

This invention relates to methods for the preparation of α, β-unsaturated ketones represented by general formula (II) (hereinafter referred to as Compound II)

$$RCH=CHCCH_3 \atop \phantom{RCH=CHC}\|\phantom{CH_3} \atop \phantom{RCH=CHC}O\phantom{CH_3}$$ (II)

where R is an aliphatic group having a side chain at the 1 position, an alicyclic group which may have substituents, a heterocyclic group which may have substituents or a phenyl group which may have substituents, which are important as intermediates for pharmaceuticals and agricultural chemicals, and to methods for the preparation of β-hydroxyketones represented by general formula (I) (hereinafter referred to as Compound I)

$$RCHCH_2CCH_3 \atop \phantom{R}|\phantom{CHCH_2}\|\phantom{CH_3} \atop \phantom{R}OH\phantom{CH}O\phantom{CH_3}$$ (I)

(where R is as defined above), which are synthetic intermediates for the said compound.

DESCRIPTION OF RELATED ART

Conventionally known methods for the preparation of Compound II include a method by aldol condensation of aldehyde with acetone [described in such documents as Ber. 40 4764 (1907)], a method by condensing aldehyde with acetone using piperidine-acetic acid as a catalyst [described in such documents as Indian J. Chem. 16B 970-972 (1978)], or a method by reacting aldehyde with metal salt of acetoacetic acid (Japanese open patent No. Sho 57-4930). However, when aldehyde with no α-hydrogen or with one α-hydrogen is used as a material, the said methods are inappropriate as industrial manufacturing methods because of low yield due to a large amount of byproducts produced usually or slow reaction, etc.

Existing methods by dehydrating β-hydroxyketones cannot be employed industrially because of various problems if they are applied to β-hydroxyketone with one γ-hydrogen in particular.

For instance, a large amount of such an expensive compound as oxalic acid is required in the reaction, in water, using a dicarboxylic acid catalyst such as oxalic acid (described in such documents as West German patent No. 840,090). It has a problem from the economical viewpoint.

In the reaction using a strong acid catalyst such as sulfuric acid, in water and acetone (described in such documents as West German open patent No. 2,426,039), a large amount of β-hydroxyketones remain and of by products, particularly β, γ-unsaturated ketones, are produced in a large quantity.

In the reaction using p-toluenesulfonic acid catalyst in an organic solvent such as benzene [described in such documents as J. Am. Chem. Soc. 81 628-632 (1959)], the reaction proceeds smoothly by azeotropicdehydration. However, isomerization from α, β-unsaturated ketones to β, γ-unsaturated ketones suddenly increase at around the end point of the reaction. Therefore it is difficult to control the β, γ-unsaturated ketones.

Known methods for the preparation of β-hydroxyketones include methods by synthesizing by aldol condensation of aldehyde with acetone [Ber. 40 4764 (1907), Ann. Chim. (Paris) 6 406-86 (1951)], and methods by reacting aldehyde with alkaline metal salt of acetoacetic acid (Japanese open patent No. Sho 55-141429). Generally the yield is low. The latter, in particular, has low yield when aldehyde with one α-hydrogen is used.

The object of this invention is to provide preparation methods for β-hydroxyketones which can be used in particular for aldehyde with one α-hydrogen, which is a drawback of the above methods, and preparation methods for obtaining α, β-unsaturated ketones from the said β-hydroxyketones with high yield.

SUMMARY OF THE INVENTION

The inventors carried out various studies to accomplish the above object, and found that it is possible to easily produce corresponding β-hydroxyketones even if aldehyde with one α-hydrogen is used with high yield by a gentle reaction in an aqueous solution in the presence of perhydroisoindole and/or pyrrolidine which may have substituents and that the said β-hydroxyketones are reacted in the presence of acid catalyst in a 2-phase system of water and water-insoluble organic solvent so as to give the intended α, β-unsaturated keytones. Thus this invention has been completed, that is, this invention is (1) A method for the preparation of α, β-unsaturated ketones represented by general formula (II)

$$RCH=CHCCH_3 \atop \phantom{RCH=CHC}\|\phantom{CH_3} \atop \phantom{RCH=CHC}O\phantom{CH_3}$$ (II)

(where R is as defined above) which comprises reacting β-hydroxyketones represented by general formula (I)

$$RCHCH_2CCH_3 \atop \phantom{R}|\phantom{CHCH_2}\|\phantom{CH_3} \atop \phantom{R}OH\phantom{CH}O\phantom{CH_3}$$ (I)

(where R is as defined above) in the presence of acid catalyst in a mixture solvent of water and water-insoluble organic solvent.

(2) A method for the preparation of α, β-unsaturated ketones represented by general formula (II)

$$RCH=CHCCH_3 \atop \phantom{RCH=CHC}\|\phantom{CH_3} \atop \phantom{RCH=CHC}O\phantom{CH_3}$$ (II)

(where R is as defined above) which comprises that aldehydes represented by general formula (III)

RCHO (III)

and acetone are reacted in the presence of one or two or more compounds selected from the group consisting of perhydroisoindole and pyrrolidine which may have substituents as catalysts, in a water solvent, at −40° C. to 60° C., then acetone is distilled to remove, and a water-insoluble organic solvent is added to the remaining reaction solution to react in the presence of acid catalyst.

(3) A method for the preparation of β-hydroxyketones represented by general formula (I)

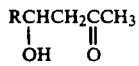 (I)

(where R is as defined above) which comprises that aldehydes represented by general formula (III)

RCHO  (III)

and acetone are reacted in the presence of one or two or more compounds selected from the group consisting of perhydroisoindole and pyrrolidine which may have substituents as catalysts, in a water solvent, at −40° C. to 60° C.

DESCRIPTION OF THE PREFERRED EMBODIMENTS

The preparation methods of this invention are illustrated by reaction equations as follows.

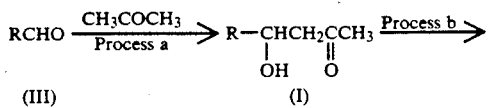

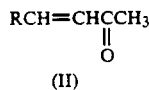

(II)

Aldehydes represented by general formula (III) (hereinafter referred to as Compound III)

RCHO  (III)

(where R is as defined above), used in Process a include aldehydes with side chain at the α position such as isobutanal, 2-methylbutanal, 2,2-dimethylpropanal, 2-methylpentanal, 2,2-dimethylbutanal, 2,3-dimethylbutanal, 2-methylhexanal, 2-ethylpentanal, 2,2-dimethylpentanal, 2,3-dimethylpentanal, 2,4-dimethylpentanal, 2-ethyl-3-methylbutanal, 2-ethyl-2-methylbutanal, 2-methylpeptanal and 2-methyloctanal; alphatic aldehydes such as cyclohexane carbaldehyde, 2-methylcyclohexane carbaldehyde, 3-methylhexane carbaldehyde and 4-methylhexane carbaldehyde; heterocyclic aldehydes such as 3-formyltetrahydropyran, 4-formyltetrahydropyran, 3-formyltetrahydrothiopyran, 3-formyltetrahydrofuran, 2-formyldioxane and 3-formylpiperidine; benzaldehydes such as benzaldehyde, p-methylbenzaldehyde, p-methylthiobenzaldehyde, p-chlorobenzaldehyde and p-nitrobenzaldehyde; or benzaldehydes with substituents. Compounds used as catalysts are pyrrolidine represented by the following formula, which may be substituted, (hereinafter referred to as the pyrrolidines)

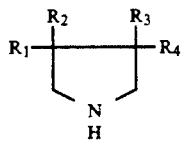

where, $R_1$, $R_2$, $R_3$ and $R_4$ are hydrogen or lower alphatic groups in addition to perhydroisoindole.

Concrete examples of the pyrrolidines include pyrrolidine, and pyrrolidines substituted at the 3 and/or 4 positions such as 3-methylpyrrolidine, 3-ethylpyrrolidine, 3,3-dimethylpyrrolidine, 3,3-diethylpyrrolidine, 3,4-dimethylpyrrolidine and 3,4-diethylpyrrolidine.

Two or more of these catalysts may be used by mixing. The reaction carried out by mixing, to a mole of Compound III, 1.5 to 20 times moles, preferably 3 to 10 times moles, of acetone; 50 to 2000 ml, preferably 200 to 500 ml, of water; and 0.002 to 0.01 moles, preferably 0.01 to 0.05 moles, of catalysts of pyrrolidines.

As for a mixing method, Compound III and acetone are mixed in an aqueous solvent, to which catalysts are added. However the method that acetone and catalysts are mixed in an aqueous solution, to which Compound III is dropped is preferable from the viewpoint of reduction in byproduct ratio of impurities represented by general formula

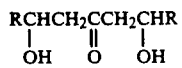

A dropping time is preferably 1 to 5 hours, and followed by curing for 1 to 7 hours. A reaction temperature differs depending on a material aldehyde used, because of equilibrium reaction. The temperature is 0° to 60° C., preferably 20° to 40° C., for aldehydes with side chain at the α position, aliphatic aldehydes or heterocyclic aldehydes. For benzaldehyde and substituted benzaldehydes, the temperature is −40° to 30° C., preferably −20° to 10° C. When a substituted benzaldehyde is used, the more the substituents are electron donative, the more the equilibrium shifts to the material system, and thus the reaction should be carried out at a lower temperature.

After the reaction is completed, the solution is neutralized with such as hydrochloric acid to make pH 1 to 6, acetone is distilled up to distillation temperature 100° C., and the obtained is used as it is for the next Process b, or, if Compound I is collected, it is extracted with water-insoluble organic solvent such as chloroform or benzene, and the extract is concentrated and distilled under vacuum, to give the intended product.

To carry out the reaction of Process b, when the aqueous solution obtained in the said Process a is used, sulfuric acid, if used as an acid catalyst, is added to the said aqueous solution so as to be an aqueous solution of 10 to 60% by weight of sulfuric acid, and hydrochloric acid, if used, is added so as to be an aqueous solution of 3 to 20% by weight of hydrochloric acid.

After it, 200 to 2000 ml, preferably 300 to 600 ml, of organic solvent is added to reflux for 0.5 to 10 hours.

When isolated Compound I is used, 200 to 2000 ml, preferably 300 to 600 ml, of organic solvent is added to 1 mole of Compound I. 50 to 1000 g, preferably 200 to 400 g, of aqueous solution of 10 to 60% by weight of sulfuric acid is added if sulfuric acid is used as an acid catalyst, or 50 to 1000 g, preferably 200 to 400 g, of aqueous solution of 3 to 20% by weight of hydrochloric acid, if hydrochloric acid is used, and the resulting solution is refluxed for 0.5 to 10 hours.

The concentration of acid catalyst is affected by type of solvent used. Generally, the concentration is made high if a refluxing temperature is low.

After the reaction is completed, the solution is separated and, 100 to 500 g of water is added to the organic solvent layer to neutralize to pH 2 to 9 with alkaline aqueous solution such as aqueous NaOH solution, then the resulting solution is separated into a water layer and an organic solvent layer.

The obtained organic solvent layer is concentrated and distilled under vacuum to give the intended Compound II.

In addition to sulfuric acid and hydrochloric acid, such acids as phosphoric acid and oxalic acid can be used for dehydration as an acid catalyst, but phosphoric acid and oxalic acid are weak acids so that a large amount is required, being inappropriate from the economical viewpoint.

A mixture solvent of water and water-insoluble organic acid which can form an aqueous layer and an organic solvent layer is used as a catalyst. Halogenated hydrocarbon solvents such as chloroform and dichloroethane, and aromatic hydrocarbon solvents such as benzene, toluene and xylene are used as the said water-insoluble organic solvent.

EXAMPLES

This invention is further described in detail by reference to the following examples. The range of this invention is not limited at all by the following examples.

EXAMPLE 1

Into a reaction vessel of 1 l in inside volume were placed 290.5 g (5 moles) of acetone, 300 ml of water and 2.2 g (0.03 moles) of pyrrolidine, to which 72.1 g (1 mole) of isobutylaldehyde was dropped over an hour while being kept at 30° C., and then stirred at 30° C. for 2 hours.

After the reaction is completed, the solution was made pH 4 with 35% hydrochloric acid, and heated to distill acetone up to distillation temperature 100° C. 325.4 g of aqueous acetone solution was obtained as distillate. An analysis of the aqueous acetone solution by gas chromatography showed 221.6 g of acetone (recovery: 76.3%. Recovery was 95.4% if a mole of acetone was regarded to be used for the reaction) and 103.8 g of water.

After it, the remaining solution after the aqueous acetone solution was distilled was cooled and extracted with 200 ml of chloroform twice. The chloroform layers were concentrated. The obtained oily product was distilled under reduced pressure to give 113.3 g of colorless oily product with boiling point of 80° to 83° C. at 12 mmHg and $n_D^{16.5}$ 1.4379 (crude yield: 87.0%)

The product was analyzed by gas chromatography to find that the intended product, 4-hydroxy-5-methylhexane-2-one was 95.1% in purity (yield: 82.7% to isobutylaldehyde used).

To the distilled aqueous acetone solution were added 68.9 g of acetone and 196.2 g of water, then 2.2 g of pyrrolidine. The same operation as the above was repeated to give the same result.

EXAMPLES 2 to 13

Example 1 was repeated except that the reaction was carried out using a different aldehyde and catalysts under conditions shown in Table 1. The results are shown in Table 1, including that of Example 1.

TABLE 1

| No. Compound | Material RCHO | Product R—CH(OH)—CH$_2$CCH$_3$(=O) | Amine as catalyst (mole ratio amine/aldehyde) | While aldehyde being dropped Temperature (°C.) Time (hr) | Completion Temperature (°C.) Time (hr) | Yield to used raw materials aldehyde (%) | Physical Properties |
|---|---|---|---|---|---|---|---|
| 1 | (CH$_3$)$_2$CH— | | pyrrolidine 0.03 | 30 / 1 | 30 / 2 | 82.7 | bp. 81~83° C. (12 mm Hg) $n_D^{14.5}$ 1.4379 |
| 2 | CH$_3$CH$_2$CH$_2$CH$_2$CH(C$_2$H$_5$)— | | 3-methylpyrrolidine 0.05 | 50 / 2 | 50 / 6 | 82.3 | bp. 87~89° C. (1 mm Hg) $n_D^{26}$ 1.4478 |
| 3 | cyclohexyl-H | | 3,3-dimethylpyrrolidine 0.03 | 30 / 1 | 30 / 3 | 94.7 | bp. 83~86° C. (0.6 mm Hg) $n_D^{17.5}$ 1.4762 |
| 4 | tetrahydropyran-O | | pyrrolidine 0.025 | 30 / 1 | 30 / 4 | 85.3 | bp. 131~135° C. (4 mm Hg) $n_D^{30}$ 1.4737 |
| 5 | tetrahydropyran-O | | pyrrolidine 0.03 | 30 / 1 | 30 / 3 | 87.2 | bp. 102~105° C. (2 mm Hg) $n_D^{27}$ 1.4736 |
| 6 | tetrahydropyran-O | | 3-methylpyrrolidine 0.03 | 30 / 1 | 30 / 4 | 88.3 | bp. 93~96° C. (2 mm Hg) $n_D^{25}$ 1.4716 |
| 7 | tetrahydrofuran-O | | pyrrolidine 0.05 | 30 / 1 | 30 / 3 | 90.4 | bp. 90~93° C. (2 mm Hg) $n_D^{24}$ 1.4670 |

TABLE 1-continued

| No. Compound | Material RCHO | Product R—CH(OH)—CH$_2$C(=O)CH$_3$ (R) | Amine as catalyst (mole ratio amine/aldehyde) | While aldehyde being dropped Temperature (°C.) Time (hr) | Completion Temperature (°C.) Time (hr) | Yield to used raw materials aldehyde (%) | Physical Properties |
|---|---|---|---|---|---|---|---|
| 8 | | tetrahydrothiopyranyl (S-containing ring) | pyrrolidine 0.01 | 30 / 3 | 30 / 4 | 93.8 | bp. 129~131° C. (0.01 mm Hg) $n_D^{31.5}$ 1.5181 |
| 9 | | phenyl | perhydroisoindole 0.03 | 5 / 1 | 5 / 1 | 91.5 | bp. 101.5~102.5° C. (0.7 mm Hg) $n_D^{16}$ 1.5316 |
| 10 | | CH$_3$—C$_6$H$_4$— | 3,4-dimethylpyrrolidine 0.05 | 5 / 1 | −5~−15 / 5 | 93.5 | bp. 101~102° C. (0.03 mm Hg) $n_D^{17}$ 1.5517 |
| 11 | | Cl—C$_6$H$_4$— | 3-ethylpyrrolidine 0.03 | −5 / 1 | −5 / 1 | 95.1 | bp. 122° C. (0.7 mm Hg) $n_D^{18}$ 1.5429 |
| 12 | | O$_2$N—C$_6$H$_4$— | perhydroisoindole 0.01 | −5 / 1 | −5 / 2 | 92.8 | mp. 57~62° C. |
| 13 | | CH$_3$S—C$_6$H$_4$— | pyrrolidine 0.03 | −5 / 1 | −6 / 15 | 95.9 | mp. 81~82° C. |

EXAMPLE 14

Into a reaction vessel of 1 l in inside volume were placed 130.2 g (1 mole) of 4-hydroxy-5-methyl-2-hexanone. 400 ml of toluene and 300 g of 20% by weight aqueous H$_2$SO$_4$ solution to heat to reflux for 3 hours. After the reaction was completed, the solution was cooled down to room temperature, and the aqueous layer was separated to remove. 150 ml of water was added to the organic layer, the pH was adjusted to 4.5 with 28% aqueous NaOH solution, and the toluene and aqueous layers were separated. The toluene layer was concentrated. The obtained oily product was distilled under reduced pressure to give 110.5 g of light yellow oily product with boiling point of 64° to 67° C. (30 mmHg) and $n^{19}_D$ 1.4428 (crude yield: 98.5%).

An analysis of the obtained product be gas chromatography revealed the intended product 5-methyl-3-hexene-2-one of 94.4% in purity. (Yield: 93.0%, to 4-hydroxy-5-methyl-2-hexanone). An amount of remaining non-reacted 4-hydroxy-5-methyl-2-hexanone was less than 0.1% and an amount of byproduct 5-methyl-4-hexene-2-one was 4.0%.

EXAMPLE 15 to 26

Example 14 was repeated except using different hydroxyketone under the conditions shown in Table 2. The results are shown in Table 2, including that of example 14.

TABLE 2

| No Compound | Material RCHCH$_2$CCH$_3$ (OH)(O) R | Product RCH=CHCCH$_3$ (O) | Solvent (ml/mole) | Aqueous acid solution (g/mole) | Reflux time (hr) | Yield (%) to material | Physical property value | non-reacted material (%) | βγ product (%) |
|---|---|---|---|---|---|---|---|---|---|
| 14 | CH$_3$)$_2$CH— | | toluene 400 ml | 20% H$_2$SO$_4$ 300 g | 3 | 93.0 | bp. 64~67° C. (30 mm Hg) $n_D^{19}$ 1.4428 | less than 0.1 | 4.0 |
| 15 | CH$_3$CH$_2$CH$_2$CH$_2$CH(C$_2$H$_5$)— | | toluene 400 ml | 5% HCl 300 g | 4 | 95.3 | bp. 85~88° C. (2 mm Hg) $n_D^{23}$ 1.4524 | 0.8 | less than 0.1 |

TABLE 2-continued

Material: RCHCH₂CCH₃ with OH and =O → $RCHCH_2C(=O)CH_3$
Product: RCH=CHCCH₃ → $RCH=CHC(=O)CH_3$

| No Compound | R | Solvent (ml/mole) | Aqueous acid solution (g/mole) | Reflux time (hr) | Yield (%) to material | Physical property value | non-reacted material (%) | βγ product (%) |
|---|---|---|---|---|---|---|---|---|
| 16 | cyclohexyl (with H) | toluene 400 ml | 5% HCl 400 g | 4 | 96.0 | bp. 80~82° C. (1 mm Hg) $n_D^{20}$ 1.4858 | 0.9 | 1.4 |
| 17 | 2-tetrahydropyranyl (O in ring) | toluene 400 ml | 20% H₂SO₄ 300 g | 3 | 92.5 | bp. 91~95° C. (0.1 mm Hg) mp. 45~46° C. | 0.3 | 2.4 |
| 18 | 1,3-dioxan-2-yl | toluene 400 ml | 20% H₂SO₄ 300 g | 2 | 96.5 | bp. 102~103° C. (2 mm Hg) $n_D^{26}$ 1.4783 | 0.1 | 1.3 |
| 19 | tetrahydropyranyl | chloroform 400 ml | 5% HCl 400 g | 4 | 94.2 | bp. 92~93° C. (5 mm Hg) $n_D^{25}$ 1.4709 | 0.3 | 1.8 |
| 20 | tetrahydrofuran-2-yl | toluene 400 ml | 20% H₂SO₄ 300 g | 2 | 93.8 | bp. 78~81° C. (3 mm Hg) $n_D^{25}$ 1.4820 | 0.4 | 1.5 |
| 21 | thianyl (S in ring) | toluene 400 ml | 20% H₂SO₄ 300 g | 3 | 95.0 | bp. 107~108° C. (0.1 mm Hg) $n_D^{32}$ 1.5320 | 1.5 | 1.3 |
| 22 | phenyl | toluene 400 ml | 20% H₂SO₄ 300 g | 2.5 | 93.2 | bp. 81~95° C. (0.6 mm Hg) mp. 41~42° C. | less than 0.1 | — |
| 23 | 4-methylphenyl (CH₃-C₆H₄-) | toluene 400 ml | 20% H₂SO₄ 300 g | 2 | 89.5 | bp. 96~103° C. (0.7 mm Hg) | 4.9 | — |
| 24 | 4-chlorophenyl (Cl-C₆H₄-) | chloroform 400 ml | 40% H₂SO₄ 300 g | 4 | 90.0 | bp. 105~108° C. (0.7 mm Hg) mp. 58~59 | 2.3 | — |
| 25 | 4-nitrophenyl (O₂N-C₆H₄-) | toluene 400 ml | 20% H₂SO₄ 300 g | 3.5 | 94.3 | mp. 106~110° C. | less than 0.1 | — |
| 26 | 4-methylthiophenyl (CH₃S-C₆H₄-) | toluene 400 ml | 10% HCl 400 g | 3 | 91.7 | mp. 103.5~106° C. | less than 0.1 | — |

EXAMPLE 27

Into a reaction vessel of 1 l in inside volume were placed 290.5 g (5 moles) of acetone, 300 ml of water and 2.1 g (0.03 moles) of pyrrolidine, to which 72.1 g (1 mole) of isobutylaldehyde was dropped over an hour which being kept at 30° C. for 1.5 hours.

After the reaction was completed, the solution was made pH 4.5 with C-sulfuric acid, and heated to distill up to distillation temperature 100° C. 323.3 g of aqueous acetone solution was obtained as distillate. An analysis of the aqueous acetone solution by gas chromatography showed 220.8 g of acetone (recovery: 76.0% Recovery was 95.0% if a mole of acetone was regarded to be used for the reaction) and 102.5 g of water.

After it, to the residue, 400 ml of chloroform and 170.1 g of C-hydrochloric acid were added and the mixture was refuxed for 2 hours. After the reaction, the reaction mixture was cooled to room temperature and the aqueous solution layers were removed and to the chloroform layers, 150 ml of water was added. After the mixture was made pH 4.5 with 28% NaOH, the chloroform layers were separated and concentrated. The obtained oily product was distilled under reduced pressure to give 92.3 g of light yellow oily product with boiling point of 61° to 64° C. at 28 mmHg and $n_D^{16.5}$ 1.4439 (crude yield: 82.3%)

The product was analyzed by gas chromatography to find that the intended product was 95.1% in purity.

EXAMPLES 28 TO 39

Example 27 was repeated except that the reaction was carried out using a different aldehyde under conditions shown in Table 3. The results are shown in Table 3, including that of Example 27.

TABLE 3

| Material RCHO | R Product R—CH=CH—CCH$_3$ ‖ O | Amine as catalyst (mole ratio amine/aldehyde) | While aldehyde being dropped temperature (°C.) time (hr) | Completion temperature (°C.) time (hr) | Adding solvent for dehydoration (ml/mole) | Aquious acid solution for dehydoration (g/mole) | Reflux time (hr) | yield |
|---|---|---|---|---|---|---|---|---|
| 27 | CH$_3$\CH—/CH$_3$ | pyrrolidine 0.03 | 30 1 | 30 1.5 | chloroform 400 | 35% HCl 170 g | 2 | 78.4 |
| 28 | CH$_3$CH$_2$CH$_2$CH$_2$CH— \| C$_2$H$_5$ | perhydro-isoindole 0.05 | 30 1 | 30 7 | toluene 400 | 95% H$_2$SO$_4$ 59 g | 3 | 80.2 |
| 29 | (cyclohexyl, H) | 3,3-dimethyl-pyrrolidine 0.03 | 30 1 | 30 3 | toluene 400 | 95% H$_2$SO$_4$ 59 g | 3 | 91.0 |
| 30 | (tetrahydropyran-2-yl) | pyrrolidine 0.03 | 30 1 | 30 3 | toluene 400 ml | 95% H$_2$SO$_4$ 60 g | 3 | 83.6 |
| 31 | (tetrahydropyran-3-yl) | pyrrolidine 0.05 | 30 1 | 30 2 | toluene 400 ml | 95% H$_2$SO$_4$ 60 g | 3 | 88.2 |
| 32 | (tetrahydropyran-4-yl) | 3-ethylpyrrolidine 0.05 | 30 1 | 30 3 | chloroform 400 ml | 35% HCl 70 g | 5 | 87.3 |
| 33 | (tetrahydrofuran-2-yl) | pyrrolidine 0.05 | 30 1 | 30 3 | toluene 400 ml | 95% H$_2$SO$_4$ 60 g | 2 | 89.7 |
| 34 | (tetrahydrothiopyran-2-yl) | pyrrolidine 0.03 | 30 1 | 30 5 | toluene 400 ml | 95% H$_2$SO$_4$ 59 g | 3 | 90.0 |
| 35 | (phenyl) | 3-methyl-pyrrolidine 0.03 | 5 1 | 5 1 | toluene 400 ml | 95% H$_2$SO$_4$ 60 g | 2 | 89.8 |
| 36 | (phenyl) | 3,4-dimethyl-pyrrolidine 0.05 | 5 1 | −5∼−15 5 | chloroform 400 ml | 20% H$_2$SO$_4$ 84 g | 2 | 83.7 |
| 37 | (4-chlorophenyl) | pyrrolidine 0.03 | −5 1 | −5 1 | toluene 400 ml | 95% H$_2$SO$_4$ 63 g | 4 | 85.6 |

TABLE 3-continued

| Material RCHO | R Product R—CH=CH—CCH₃ ‖ O | Amine as catalyst (mole ratio amine/aldehyde) | While aldehyde being dropped temperature (°C.) time (hr) | Completion temperature (°C.) time (hr) | Adding solvent for dehydoration (ml/mole) | Aquious acid solution for dehydoration (g/mole) | Reflux time (hr) | yield |
|---|---|---|---|---|---|---|---|---|
| 38 | 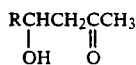 O₂N— | perhydro-isoindole 0.01 | −5 1 | −5 2 | toluene 400 ml | 95% H₂SO₄ 59 g | 3 | 98.3 |
| 39 | 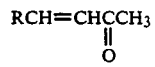 CH₃S— | pyrrolidine 0.03 | −5 1 | −6 1.5 | toluene 400 ml | 35% HCl 114 g | 3 | 89.8 |

INDUSTRIAL APPLICABILITY

This invention provides economically advantageous methods for the preparation of the intended β-hydroxyketones (Compound I) and α,β-unsaturated ketones (Compound II) from an aldehyde with no α-hydrogen or with one α-hydrogen with high yield under gentle reaction conditions, being extremely significant in industry.

We claim:

1. Method for preparing α,β-unsaturated ketone which comprises:

(1) dehydrating a β-hydroxyketone of the formula (I)

$$\underset{\underset{OH}{|}\;\;\underset{O}{\|}}{RCHCH_2CCH_3} \quad (I)$$

wherein R is (i) an aliphatic group having a side chain at the 1 position, (ii) an alicyclic group optionally substituted, (iii) a heterocyclic group optionally substituted; or (iv) a phenyl group optionally substituted;

(2) in the presence of an acid catalyst in a solvent mixture comprising water and a water-insoluble organic solvent compound (3) under conditions sufficient to thereby produce a α,β-unsaturated ketone of the formula (II)

$$\underset{\underset{O}{\|}}{RCH{=}CHCCH_3} \quad (II)$$

wherein R is as defined above.

2. Method for preparing α,β-unsaturated ketone which comprises:

(1) reacting an aldehyde of the formula (III)

$$RCHO \quad (III)$$

wherein R is (i) an aliphatic group having a side chain at the 1 position, (ii) an alicyclic group optionally substituted, (iii) a heterocyclic group optionally substituted, or (iv) a phenyl group optionally substituted;

(2) with acetone, (3) utilizing a catalyst comprising perhydroisoindole or pyrrolidine or mixtures thereof, (4) in the presence of water, (5) under condensation conditions sufficient to thereby produce a β-hydroxyketone of the formula (I)

$$\underset{\underset{OH}{|}\;\;\underset{O}{\|}}{RCHCH_2CCH_3} \quad (I)$$

wherein R is as defined above, and to remove unreacted acetone therefrom;

(6) dehydrating the β-hydroxyketone (7) utilizing an acid catalyst in a solvent mixture comprising water and a water-insoluble organic solvent compound, (8) under conditions sufficient to thereby produce α,β-unsaturated ketone of the formula (II)

$$\underset{\underset{O}{\|}}{RCH{=}CHCCH_3} \quad (II)$$

wherein R is as defined above.

3. Method of producing α,β-unsaturated ketone which comprises (a) admixing acetone and a catalyst comprising perhydroisoindole or pyrrolidine of the formula

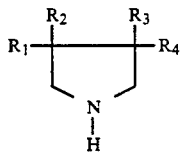

wherein R₁, R₂, R₃, and R₄ are hydrogen or lower aliphatic groups in an aqueous solvent;

(b) slowly introducing into the acetone-catalyst admixture an aldehyde of the formula

RCHO wherein R is an aliphatic group having a side chain at the 1 position, an alicyclic group optionally substituted, a heterocyclic group optionally substituted, or a phenyl group optionally substituted, under condensation conditions sufficient to react the acetone and aldehyde thereby producing an aqueous solution of corresponding β-hydroxyketone reaction product;

(c) removing unreacted acetone from the solution of reaction product;

(d) introducing an acid catalyst and a water insoluble organic solvent into the aqueous reaction product under reaction conditions to convert β-hydroxyketone into the corresponding α,β-unsaturated ketone of the formula
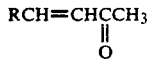
wherein R is as defined above; and,
(e) recovering α,β-unsaturated ketone in high purity.
* * * * *